US00PP18961P2

(12) United States Plant Patent
de Boer et al.

(10) Patent No.: US PP18,961 P2
(45) Date of Patent: Jun. 24, 2008

(54) ***ERYNGIUM* PLANT NAMED 'SUNNY JACKPOT'**

(50) Latin Name: *Eryngium planum*
Varietal Denomination: Sunny Jackpot

(76) Inventors: Huibert Anne de Boer, Collegiantenstraat 90, 2231 HM Rijnsburg (NL); René van Gaalen, Sionsweg 26, 2286 KL Rijswijk (NL)

( * ) Notice: Subject to any disclaimer, the term of this patent is extended or adjusted under 35 U.S.C. 154(b) by 0 days.

(21) Appl. No.: 11/725,796

(22) Filed: Mar. 20, 2007

(51) Int. Cl.
*A01H 5/00* (2006.01)

(52) U.S. Cl. ..... Plt./361
(58) Field of Classification Search ..... Plt./361
See application file for complete search history.

*Primary Examiner*—Annette H Para
(74) *Attorney, Agent, or Firm*—C. A. Whealy

(57) ABSTRACT

A new and distinct cultivar of *Eryngium* plant named 'Sunny Jackpot', characterized by its upright and inverted triangular plant habit; moderately vigorous growth habit; green and yellow green variegated foliage; and flower heads with green and blue-colored flowers.

2 Drawing Sheets

Botanical designation: *Eryngium planum.*
Cultivar denomination: 'Sunny Jackpot'.

BACKGROUND OF THE INVENTION

The present invention relates to a new and distinct cultivar of *Eryngium* plant, botanically known as *Eryngium planum,* and hereinafter referred to by the name 'Sunny Jackpot'.

The new *Eryngium* was discovered by the Inventors in a controlled environment in Rijnsburg, The Netherlands, in July, 2005, as a naturally-occurring whole plant mutation of the *Eryngium planum* cultivar Blue Dream, not patented. The new *Eryngium* was observed as a single plant from within a population of plants of the cultivar Blue Dream. The selection of this plant was based on its unique variegated foliage.

Asexual reproduction of the new *Eryngium* by cuttings in a controlled environment in Rijnsburg, The Netherlands since July, 2005, has shown that the unique features of this new *Eryngium* are stable and reproduced true to type in successive generations.

SUMMARY OF THE INVENTION

The cultivar Sunny Jackpot has not been observed under all possible environmental conditions. The phenotype may vary somewhat with variations in environment such as temperature and light intensity, without, however, any variance in genotype.

The following traits have been repeatedly observed and are determined to be the unique characteristics of 'Sunny Jackpot'. These characteristics in combination distinguish 'Sunny Jackpot' as a new and distinct cultivar of *Eryngium:*

1. Upright and inverted triangular plant habit.
2. Moderately vigorous growth habit.
3. Green and yellow green variegated foliage.
4. Flower heads with green and blue-colored flowers.

Plants of the new *Eryngium* differ from plants of the parent, the cultivar Blue Dream, primarily in foliage color as plants of the cultivar Blue Dream have solid green-colored leaves.

Plants of the new *Eryngium* can also be compared to plants of the *Eryngium planum* cultivar Blue Dwarf, not patented. Plants of the new *Eryngium* differ from plants of the cultivar Blue Dwarf primarily in foliage color as plants of the cultivar Blue Dwarf have solid green-colored leaves.

BRIEF DESCRIPTION OF THE PHOTOGRAPHS

The accompanying photographs illustrate the overall appearance of the new *Eryngium.* The photographs show the colors as true as it is reasonably possible to obtain in colored reproductions of this type. Colors in the photographs may differ slightly from the color values cited in the detailed botanical description which accurately describe the colors of the new *Eryngium.*

The photograph on the first sheet comprises a side perspective view of a typical flowering plant of 'Sunny Jackpot' grown in an outdoor nursery.

The photograph at the top of the second sheet is a close-up view of a typical flowering stem of 'Sunny Jackpot'.

The photograph at the bottom of the second sheet is a close-up view of typical leaves of 'Sunny Jackpot'.

DETAILED BOTANICAL DESCRIPTION

In the following description, color references are made to The Royal Horticultural Society Colour Chart, 2001 Edition, except where general terms of ordinary dictionary significance are used. The following observations and measurements describe plants grown in Rijnsburg, The Netherlands during the late summer in an outdoor nursery and under conditions and practices which approximate those generally used in commercial *Eryngium* production. During the production of the plants, day temperatures ranged from 15° C. to 22° C. and night temperatures ranged from 6° C. to 13° C. Measurements and numerical values represent averages for typical flowering plants. Plants were about one year old when the photographs and description were taken.

Botanical classification: *Eryngium planum* cultivar Sunny Jackpot.

Parentage: Naturally-occurring whole plant mutation of the *Eryngium planum* cultivar Blue Dream, not patented.

Propagation:

*Type.*—By cuttings.

*Time to initiate roots.*—About 80 days at 12° C.

*Time to produce a rooted young plant.*—About six months at 18° C.

*Root description.*—Fibrous, fleshy and thick; white in color.

*Rooting habit.*—Freely branching; dense.

Plant description:

*Plant form/growth habit.*—Herbaceous perennial; upright and inverted triangular plant habit. Moderately vigorous growth habit.

*Plant height.*—About 58 cm.

*Plant diameter or spread.*—About 26.5 cm.

*Lateral branches.*—Length: About 8.9 cm. Diameter: About 2.5 mm. Aspect: Mostly upright to slightly outward. Strength: Strong. Texture: Smooth, glabrous. Color: 91A to 91C; towards the base, 145B.

Foliage description:

*Arrangement.*—Alternate, simple.

*Length, upper leaves.*—About 3.8 cm.

*Length, lower leaves.*—About 6.9 cm.

*Width, upper leaves.*—About 3.3 cm.

*Width, lower leaves.*—About 4.2 cm.

*Shape, upper leaves.*—Palmately lobed.

*Shape, lower leaves.*—Ovate to obovate.

*Apex, upper and lower leaves.*—Mucronulate.

*Base, upper leaves.*—Hastate.

*Base, lower leaves.*—Cordate.

*Margin, upper leaves.*—Serrate.

*Margin, lower leaves.*—Crenate.

*Texture, upper and lower leaves, upper and lower surfaces.*—Smooth, glabrous; leathery.

*Venation pattern, upper and lower leaves.*—Pinnate.

*Color, upper and lower leaves.*—Developing foliage, upper surface: 143A to 143B; towards the margins, between 149B and 150B. Developing foliage, lower surface: 143C to 143D; towards the margins, between 150C and 154C. Fully expanded foliage, upper surface: 143A; towards the margins, 150C to 150D; venation, 138C. Fully expanded foliage, lower surface: 143B to 143C; towards the margins, between 150C to 150D and 154C to 154D; venation, 138C.

*Petioles* (*only on lower leaves, upper leaves are sessile*) .—Length: About 2.6 cm. Diameter: About 3 mm. Texture, upper and lower surfaces: Smooth, glabrous. Color, upper and lower surfaces: 138B to 138C.

Flower description:

*Flower arrangement and habit.*—Single rotate flowers arranged on conical flower heads; flowers sessile. Inflorescences arising from leaf axils. Freely flowering habit with usually about 100 flowers developing per inflorescence. Flowers persistent. Flowers face upright and outwardly. Flowers not fragrant.

*Natural flowering season.*—Plants of the new *Eryngium* initiate and develop flowers during the late summer and flower continuously from August through October in The Netherlands.

*Flower longevity.*—Flowers last about two weeks on the plant.

*Inflorescence height.*—About 8.7 cm.

*Inflorescence diameter.*—About 5.9 cm.

*Flower diameter.*—About 4 mm.

*Flower length* (*depth*).—About 6 mm.

*Flower bud.*—Shape: Obovate. Length: About 1.5 mm. Diameter: About 1 mm. Color: 145B.

*Petals.*—Arrangement: Five petals in a single whorl. Length: About 3 mm. Width: About 1.5 mm. Shape: Elliptic. Apex: Acute; recurved. Margin: Entire. Texture, upper and lower surfaces: Smooth, glabrous. Color: When opening, upper and lower surfaces: 145D. Fully opened, upper and lower surfaces: 91A; towards the base, 145B; color becoming closer to 93B with development.

*Sepals.*—Arrangement: Five sepals in a single whorl. Length: About 3 mm. Width: About 1.5 mm. Shape: Ovate. Apex: Acute. Base: Cuneate. Margin: Entire. Texture, upper and lower surfaces: Smooth, glabrous. Color, immature, upper and lower surfaces: 137C; towards the base, 144C to 144D. Color, mature, upper surface: 137C; towards the base, 144C to 144D. Color, mature, lower surface: 137B.

*Inflorescence bracts.*—Arrangement: About 14 bracts in a single whorl subtending the flower head. Length: About 2.8 cm. Width: About 4 mm. Shape: Ovate. Apex: Apiculate. Base: Cuneate. Margin: Entire. Texture, upper and lower surfaces: Smooth, glabrous. Color, immature and mature, upper and lower surfaces: 96C to 96D.

*Peduncles.*—Length: About 5.1 cm. Diameter: About 2 mm. Angle: Main peduncle, about 5° from vertical; lateral peduncles, about 35° from vertical. Strength: Strong. Texture: Smooth, glabrous. Color: 90C to 90D.

*Reproductive organs.*—Stamens: Quantity/arrangement: About four per flower. Anther shape: Ovate. Anther length: About 1 mm. Anther color: 161D. Filament length: About 2.5 mm. Filament color: 91A. Pollen amount: Scarce. Pollen color: Close to 156D. Pistils: Quantity: About three per flower. Pistil length: About 3 mm. Style length: About 2.8 mm. Style color: 91D; towards the base, 91B. Stigma shape: Rounded. Stigma color: 91D. Ovary color: 144B to 144C. Fruits/seeds: Fruit and seed development have not been observed.

Disease/pest resistance: Plants of the new *Eryngium* have not been shown to be resistant to pathogens and pests common to *Eryngium*.

Garden performance: Plants of the new *Eryngium* have exhibited good tolerance to rain and wind, have been observed to tolerate temperatures from about −20° C. to about 35° C.

It is claimed:

1. A new and distinct *Eryngium* plant named 'Sunny Jackpot' as illustrated and described.

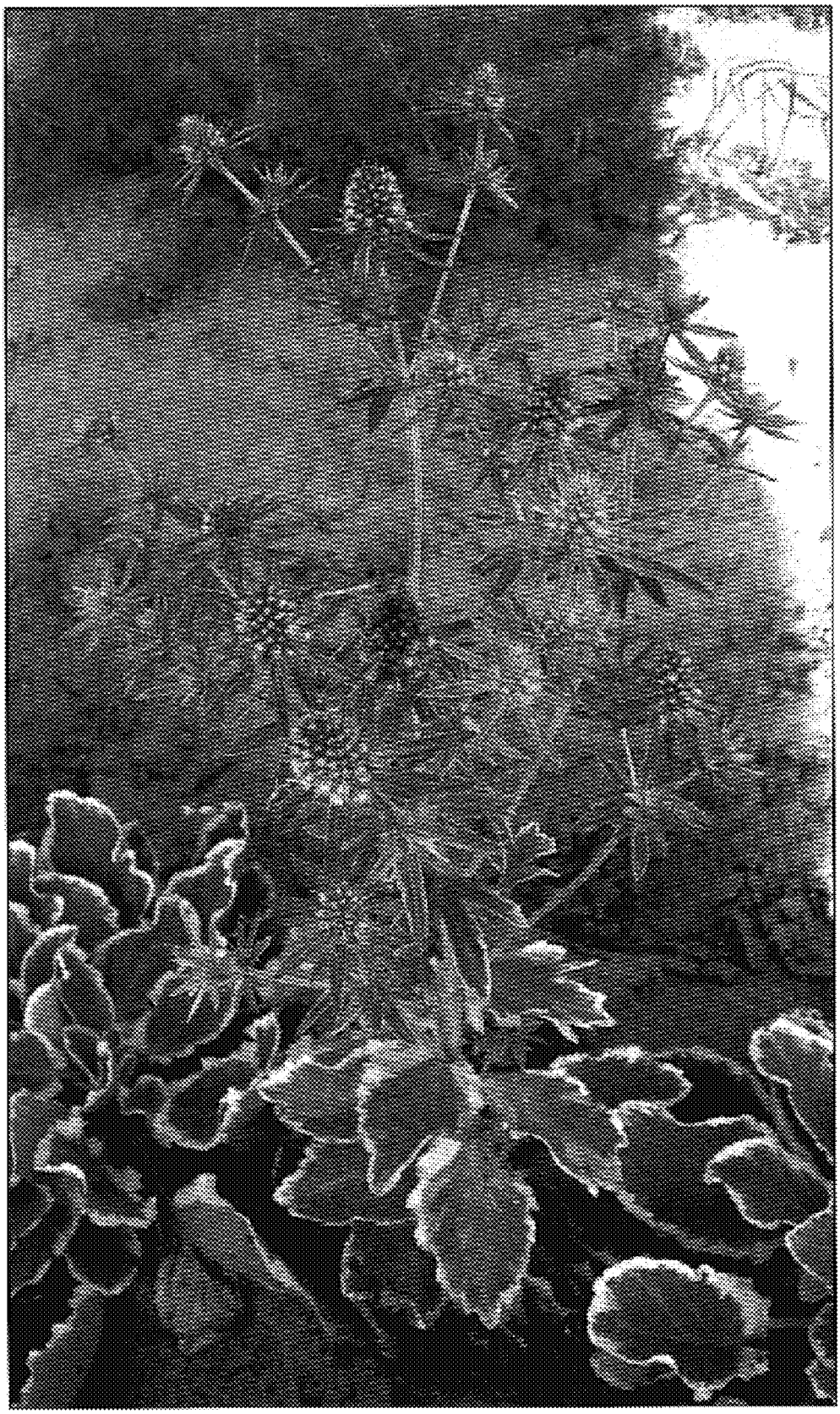

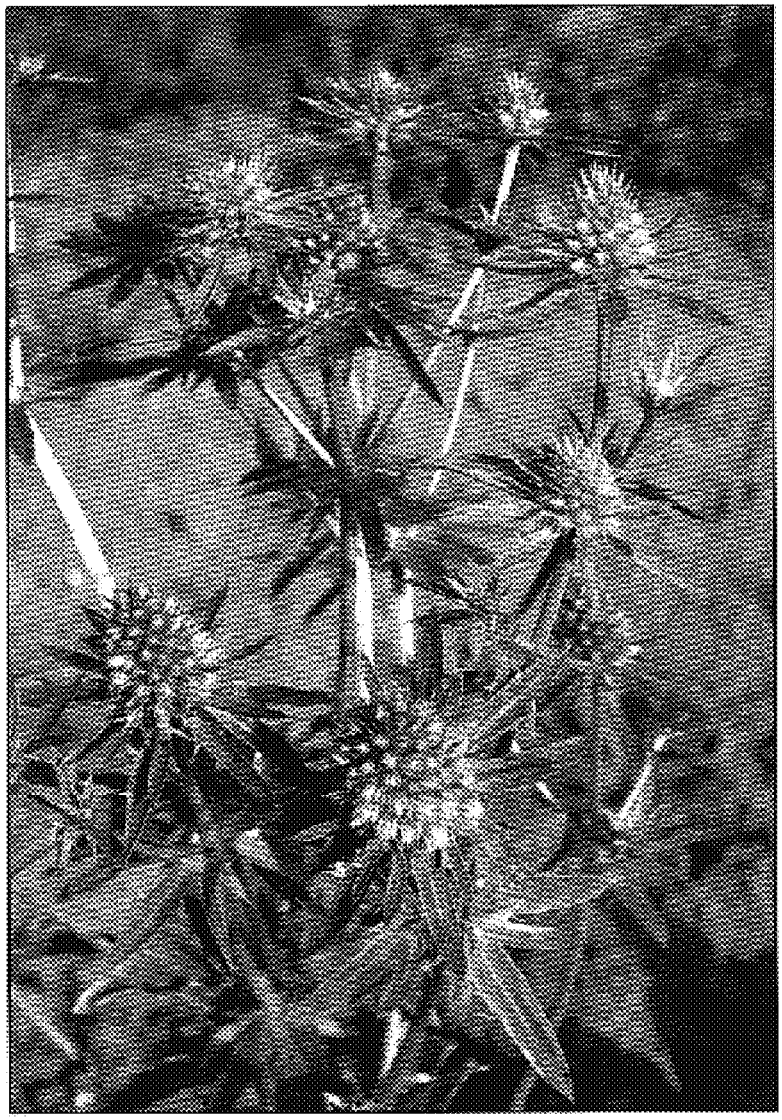
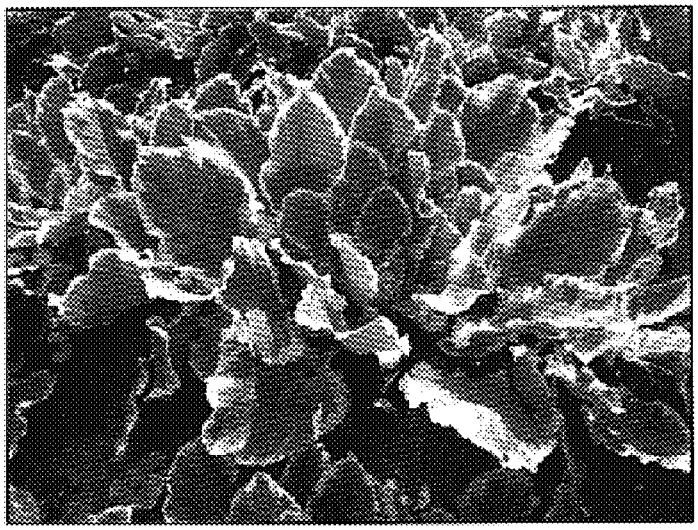

* * * * *